(12) United States Patent
Haszler et al.

(10) Patent No.: US 6,631,177 B1
(45) Date of Patent: Oct. 7, 2003

(54) DEVICE FOR MEASUREMENT OF METAL SHEET THICKNESS AND CLAD LAYER THICKNESS AND METHOD OF USE THEREOF

(75) Inventors: Alfred Johann Peter Haszler, Valendar (DE); Hormoz Ghaziary, Los Gatos, CA (US)

(73) Assignee: Corus Aluminium Walzprodukte GmbH, Koblenz (DE)

( * ) Notice: Subject to any disclaimer, the term of this patent is extended or adjusted under 35 U.S.C. 154(b) by 166 days.

(21) Appl. No.: 09/635,686

(22) Filed: Aug. 10, 2000

(30) Foreign Application Priority Data

Aug. 10, 1999 (EP) .............................. 99202608

(51) Int. Cl.⁷ .............................................. G01B 15/02
(52) U.S. Cl. ............................................ 378/50; 378/42
(58) Field of Search ............................ 378/50, 54, 44, 378/88–90, 42, 45, 46, 53

(56) References Cited

U.S. PATENT DOCUMENTS

| | | | |
|---|---|---|---|
| 2,711,480 A | * 6/1955 | Friedman | 250/51 |
| 2,926,257 A | * 2/1960 | Friedman | 250/53 |
| 3,919,548 A | * 11/1975 | Porter | 250/277 |
| 4,696,023 A | 9/1987 | Kuusi | |
| 4,764,945 A | * 8/1988 | Tadahiro | 378/50 |
| 5,113,421 A | * 5/1992 | Gignoux et al. | 378/50 |
| 5,325,416 A | * 6/1994 | Saito et al. | 378/50 |
| 5,365,563 A | 11/1994 | Kira et al. | |
| 5,406,608 A | * 4/1995 | Yellepeddi et al. | 378/46 |
| 5,579,362 A | * 11/1996 | Matsuura et al. | 378/59 |
| 6,038,280 A | * 3/2000 | Rossiger et al. | 378/50 |
| 6,173,037 B1 | 1/2001 | Brouwer | |
| 6,381,303 B1 | * 4/2002 | Vu et al. | 378/46 |

FOREIGN PATENT DOCUMENTS

| | | | |
|---|---|---|---|
| EP | 0389774 | 10/1990 | |
| JP | 61195335 | 8/1986 | |
| JP | 62137552 | 6/1987 | |
| JP | 5-209847 | * 8/1993 | ......... G01N/23/223 |

* cited by examiner

Primary Examiner—Drew A. Dunn
Assistant Examiner—Irakli Kiknadze
(74) Attorney, Agent, or Firm—Stevens, Davis, Miller & Mosher, LLP

(57) ABSTRACT

A device for the measurement of the thickness of a first layer, including one or more sublayers, on a second layer of a metal sheet by X-ray fluorescence analysis, includes (a) an X-ray source for generating and directing a beam of polychromatic primary X-rays, the beam being able to penetrate into the first and second layers for converting primary X-rays into chemical element specific fluorescent X-rays by absorption of primary X-rays and re-emission of fluorescent X-rays by the chemical element; and (b) a detector module for detecting element specific fluorescent X-rays and determining an intensity thereof. In the method of using the device, the detector module for detection is placed at an angle with respect to the primary beam of X-rays in dependence of the chemical element from which the fluorescent X-rays are to be detected. The device achieves an improvement in the efficiency of detection, and the measurement time is reduced accordingly. Hence, a device is provided with which alloys with a low concentration of fluorescent elements can now be analyzed, for determining the thickness of a cladding.

40 Claims, 5 Drawing Sheets

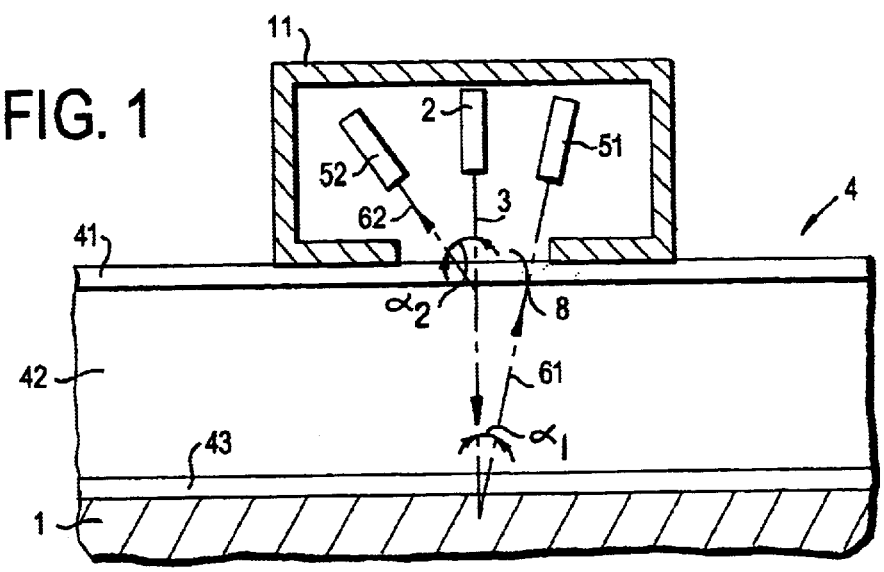
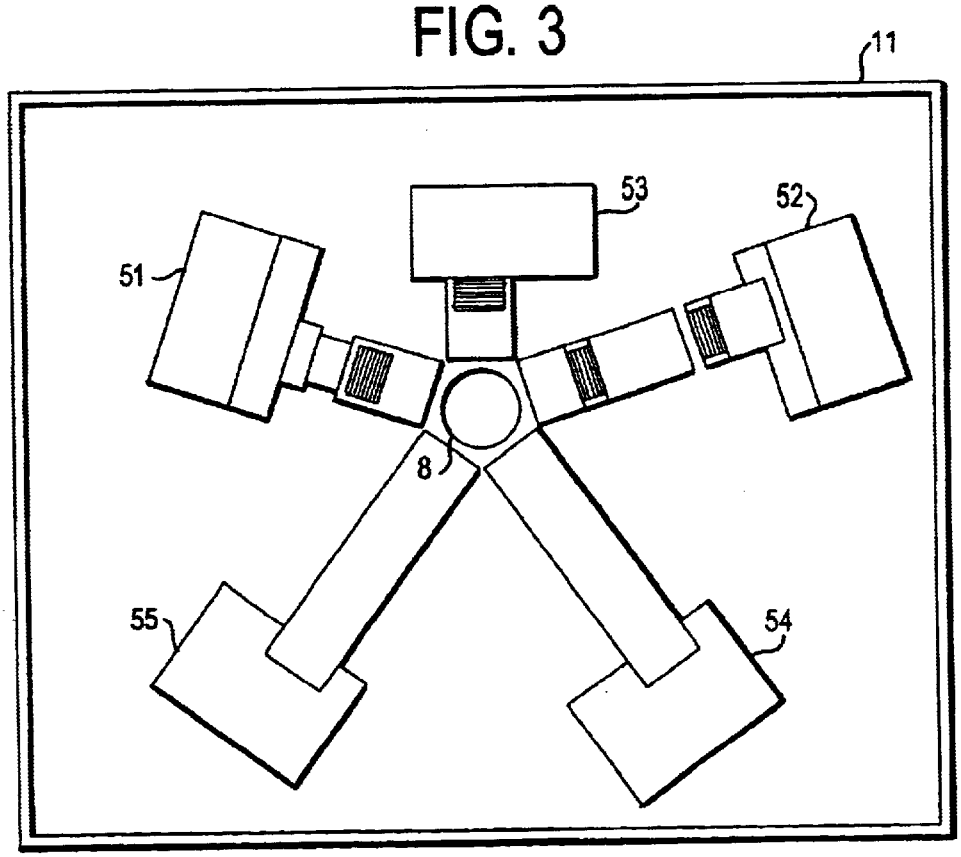

| ELEMENT | ATOMIC No. | LINE | WAVELENGTH (ANGSTROMS) | 2θ ANGLE (DEG.) +/- 0.005° |
|---|---|---|---|---|
| Mn | 25 | Kα | 2.103 | 62.97 |
| Fe | 26 | Kα | 1.937 | 57.52 |
| Cu | 29 | Kα | 1.541 | 45.03 |
| Zn | 30 | Kα | 1.436 | 41.80 |
| Mo | 42 | Kα | 0.71 | 20.33 |

| Name | Core | Min. | Cu | Zn | Fe |
|------|------|------|------|------|------|
| 3560 | Core | 4476 | 3323 | 3650 | 4950 |
| 3560 | Core | 4815 | 2359 | 4167 | 5727 |
| 3560 | Core | 4815 | 2359 | 4167 | 5727 |
| 3570 | Core | 3131 | 5740 | 3427 | 4988 |
| 3570 | Core | 3153 | 5635 | 2473 | 4783 |
| 4100 | Brazing Clad | 1776 | 4518 | 3760 | 2980 |
| 4100 | Brazing Clad | 1812 | 1676 | 4128 | 4094 |
| 4100 | Brazing Clad | 1858 | 1675 | 4140 | 4098 |
| 4100 | Brazing Cald | 246 | 1115 | 1359 | 2769 |
| 4100 | Brazing Clad | 252 | 1120 | 1375 | 2779 |
| 4100 | Brazing Clad | 2617 | 1142 | 1189 | 2678 |
| 4100 | Brazing Clad | 278 | 1533 | 1330 | 2461 |
| 4100 | Brazing Clad | 280 | 1244 | 1455 | 2519 |
| 4100 | Brazing Clad | 285 | 1015 | 1115 | 2170 |
| 4100 | Brazing Clad | 290 | 1025 | 1123 | 2190 |

FIG. 7

| Alloy | Type | % Deviation |
|-------|------|-------------|
| 4430 | Brazing Clad | 0.016 |
| 4433 | Brazing Clad | 7.459 |
| 4100 | Brazing Clad | 15.968 |

FIG. 8

DEVICE FOR MEASUREMENT OF METAL SHEET THICKNESS AND CLAD LAYER THICKNESS AND METHOD OF USE THEREOF

BACKGROUND OF THE INVENTION

1. Field of the Invention

The invention relates to a device for measurement of the thickness of a first layer, comprising one or more sublayers, on a second layer of a metal sheet by X-ray fluorescence analysis, and a method of use therefor. In particular, the device comprises means defining a specimen plane for supporting the metal sheet, and further comprises means for generating and directing a beam of polychromatic primary X-rays. The beam is able to penetrate into the first and second layers for converting primary X-rays into chemical element specific fluorescent X-rays by means of absorption of the primary X-rays and re-emission of the fluorescent X-rays by the chemical element. The device further comprises means for detecting element specific fluorescent X-rays and determining an intensity thereof.

2. Description of Related Art

An X-ray device is known from U.S. Pat. No. 2,711,480. In the known device, the beam of primary X-rays is directed at an arbitrary angle on a sheet material, and relative to the beam of primary X-rays the detection means are aligned at an arbitrary angle to receive fluorescent radiation that emanates in all directions from the sheet. The known device is applicable in a method to determine the thickness of a layer of material on a chemically different base material, by measuring the attenuation of fluorescent radiation of the most abundant element comprised in the base material in passing through the layer.

However, in many cases it is not possible to use the fluorescence of the most abundant element, in particular when dealing with metal sheets comprising layers of alloys with mutually very similar compositions. Within the scope of this description, the term "cladding" is used to denote the first layer, and the term "clad layer" is used to indicate a sublayer.

SUMMARY OF THE INVENTION

It is an object of the invention to provide a device for measurement of cladding thickness, which is capable of using fluorescence signals from elements that are present in a layer in low concentration for the thickness determination.

It is a further object of the invention to provide a device that is capable of measuring both the cladding thickness, as well as the thickness of the full metal sheet, with improved accuracy and reduced measurement time, so that the cladding thickness can be expressed as a fraction of the total metal sheet thickness.

It is a further object of the invention to provide a device for measurement of cladding thickness and metal sheet thickness with improved ease of operation, and reduced probability for operator mistakes.

It is a further object to provide a device that is suitable for use in a production environment.

It is a further object to provide a method of using the device.

According to the invention, one or more of these objects is achieved by providing a device in which the means for detection have been placed at an angle with respect to the primary beam of X-rays in dependence of the chemical element from which the fluorescent X-rays are to be detected. This achieves an improvement of the efficiency of detection, and the measurement time is reduced accordingly. Hence, a device is provided in which alloys with a low concentration of fluorescent elements can now be analysed, for determining the thickness of a cladding. In the scope of the present description, the term "detection channel" will be used to denote means for detection that have been placed to selectively receive fluorescent x-rays specific for one chemical element.

The invention is based on the finding that the fluorescent radiation emanates from a metal sheet under an exit angle that is characteristic of the wavelength of the emitted fluorescent X-rays inside a host material complex. When properly excited, chemical elements are able to emit fluorescent X-rays with a spectrum of wavelengths that is characteristic for each fluorescent element. Hence, by placing the means for detection to receive fluorescent X-rays that emanate from the surface of the metal sheet under a specific exit angle, an element selective fraction of the X-rays that emanate from the metal sheet is detected. Thus the detection means receive a pre-selection of fluorescent X-rays, in favour of the fluorescent X-rays that carry the relevant information to be quantified.

In a preferred embodiment, the device comprises at least two different detection channels placed at an angle to receive fluorescent X-rays from different chemical elements. Herewith a device is provided with high flexibility in its ability to measure a variety of types of metal sheets. Additionally, the device is flexible in its ability to take into account multiple signals of fluorescent X-rays converted in different elements. The device can thus select a signal that provides the most advantageous measurement in a given operation of thickness measurement. A further advantage of the device according to this embodiment is that for each chemical element from which fluorescence is detected it is possible to measure the thickness of an additional (sub-)layer in the metal sheet.

In a preferred embodiment, the means for directing the beam of primary X-rays has been placed such that the beam of primary X-rays is directed substantially perpendicular to the specimen plane. Herewith it is achieved that primary X-rays penetrate as deep as possible into the metal sheet to be converted into fluorescent X-rays. This geometry offers the most space along the specimen plane for additional detection channels over the full azimuthal range.

In an embodiment of the invention, the means for directing a beam of primary X-rays and the means for detecting element-specific fluorescent X-rays are integrated into one measuring unit. Herewith a single measuring unit is obtained that can be moved across for instance a large metal sheet, to analyse the metal sheet in several locations. Amongst other ways to guide the motion of the integrated unit, it is particularly advantageous to provide a set of rail members for this purpose.

In an embodiment of the invention the device comprises means for pressing the measuring unit toward the specimen plane. Accordingly, during operation of this embodiment of this device, the measuring unit can be pressed against the surface of the metal sheet under investigation. This embodiment assures that the angle of incidence and exit of X-rays with respect to the surface of the metal sheet is well defined and constant. Moreover, a close contact is achieved between the metal sheet and the means for supporting the metal sheet. As a consequence, the device with pressing means is capable of performing measurements with higher accuracy than without pressing means.

Preferably, the means for pressing is pneumatic means for pressing. A high degree of control of the pressing force is obtained using a pneumatic system. Another advantage is that a quick change is made possible between a state of pressing the unit against a body and a state of release. This enables a quick succession of measurements to be made on different areas of the sheet under investigation.

In an embodiment of the invention, the device comprises means for storing an identifying label and a corresponding standard result for a plurality of standard metal sheets, and means for processing and comparing a measurement of at least one fluorescent X-ray intensity to the standard to find the identifying label of the standard metal sheet that best matches the measurement. Such a device is capable of executing metal sheet identification. In this embodiment, the appropriate materials parameters such as layer composition can now be available for extracting the correct values for the thickness of the metal sheet and/or a cladding. By preference, intensities of a plurality of detectors are compared to corresponding standard intensities. The device can then find the best matching metal sheet identification label using the combined intensities. In many practical situations the chemistry of the layers in which the fluorescent X-rays have been converted varies from metal sheet to metal sheet. With the invention a device is provided that determines the type of metal sheet in the process of a measurement of thickness. Furthermore, a correction can be applied to the determined intensity of fluorescent X-rays, in the case that the fluorescent element is present in more than one layer. A further advantage is that the device can thus be used with minimal or no operator intervention, since the device selects from the storage means the information it needs, such as alloying constituents. Otherwise it is achieved that operator errors can be discovered. In such cases the information presented on the information unit does not match the operator's intentions. Typical operator errors are interchanging metal sheet specimens or placing the metal sheet with the wrong side facing the means for directing and detecting. In another embodiment, the device comprises an information unit for indicating the best matching standard metal sheet, or the best matching standard metal sheet as well as at least one other identification label that corresponds to a standard metal sheet that matches next best.

In a preferred embodiment, the means for supporting the metal sheet comprises a backing for converting primary X-rays into backing-specific fluorescent X-rays by means of absorption of primary X-rays and re-emission of fluorescent X-rays by the backing, wherein the backing is located such that the metal sheet is placeable between the means for generating and directing a beam of polychromatic primary X-rays and the backing. In this embodiment, a device is provided that can additionally determine the thickness of the full metal sheet by measurement of absorption of fluorescent X-rays from the backing. In certain applications it is required to express the thickness of the cladding as a fraction of the total thickness of the metal sheet. The device according to the invention can express the cladding thickness as a fraction of the total thickness of the metal sheet.

In a preferred embodiment of the device comprising a backing, the device comprises an individual detection channel for receiving fluorescent X-rays specific for the backing. This provides a device which allows for a measurement of both the cladding thickness as well as the full thickness of the metal sheet, without performing a re-alignment step when a metal sheet is inserted that is different from the previous metal sheet. In an industrial environment it is not practical to align the means for detection each time a different metal sheet is to be analysed. A further advantage of a device comprising individual detection channels is that it can simultaneously determine intensities of fluorescence emanating from the backing and of one or more chemical elements comprised in the metal sheet. Hence the device is suitable for collecting data simultaneously for determining both the full thickness of the metal sheet as well as the cladding. For each chemical element from which fluorescence is detected it is possible to measure the thickness of an additional (sub-) layer. Simultaneous detection reduces the time required for a measurement even further.

Hereafter, some embodiments of the invention will be described that offer advantages specific for measuring thicknesses in aluminum sheet. For the purpose of this application, aluminum sheet is held to comprise aluminum-alloy sheet. Currently, an important product that comprises aluminum alloy sheet material is brazing sheet. Brazing sheet is typically used in automobile radiators, air conditioner evaporators, heat exchangers, and the like. Brazing sheet is a composite material that comprises an aluminum alloy core, with on one or both sides one or more clad layers with different alloys, most often different aluminum alloys. The purpose of the cladding is to impart specific properties in the outside layer of a sheet product, such as brazing capability, corrosion resistance, erosion resistance, wear resistance, while the core alloy maintains other necessary properties such as strength.

Brazing sheet composite may be manufactured by hot rolling in which a slab of cladding material is placed to an ingot of the core material. The hot rolling process is then performed on this combination. In the final product, the core and the cladding strongly bond together, due to the fact that they are primarily of the same metal with a different content of alloying elements. Typically both core and cladding have over 80% aluminum. The process is highly delicate, and requires strict operation practices since the final sheet specification is usually rigid. Among the specifications which must be met is the cladding thickness as well as the total thickness of the brazing sheet.

Currently, these sheet specifications are measured and verified using metallographic and optical methods, involving sampling the metal sheet, preparing a metallographic mount, several steps of polishing and surface treatment, and determining the cladding and total thickness using optical microscopy. This analysis method is rather labor intensive and entails unacceptable long turn-around times of at least several hours.

To this extent, in a preferred embodiment, the backing comprises the element molybdenum. More preferably, the backing consists of essentially molybdenum. Herewith an excellent source of fluorescent X-rays is provided. The attenuation of Mo-$K_\alpha$, radiation is, relative to the detection accuracy, almost independent of aluminum alloy-composition in most aluminum alloys, which is advantageous in interpretation of a measurement. The attenuation of this radiation as it passes through the entire metal sheet of essentially aluminum alloy is low enough so that a high enough fraction reaches the detection means to measure an intensity in acceptable time, while at the same time the attenuation is sufficiently high to accurately determine. The typical range of thickness of aluminum alloy sheet, for example brazing sheet, that can be measured in this embodiment is between 0.07 mm and 6.35 mm. Moreover, molybdenum is sufficiently resistant against wear, and relatively inexpensive. Not least important is the fact that molybdenum does not typically exist in aluminum alloys, neither as alloying element, nor as a stray element. In a further preferred embodiment, the backing is permanently attached to a test surface of a measurement table, to form the specimen plane.

In a preferred embodiment, the device comprises at least a detection channel for receiving fluorescent X-rays specific for a chemical element of a group comprising Cu, Mn, Zn, Fe, in a metal layer comprising mainly Al. By this embodiment an intensity of fluorescent X-rays can be measured of an alloying element that is often used within an aluminum core alloy. The device can thus be used to determine the attenuation in a cladding, comprising a metal or an aluminum alloy, of fluorescent X-rays of alloying elements from a core layer. This, in turn, provides the information needed to determine a cladding thickness. Because of the alignment of the means for detecting according to the invention, the thickness of layers can now be determined using fluorescent X-rays even on alloys with a low concentration of fluorescent elements. Furthermore, a device is provided that can determine the thickness of a cladding comprising mainly the element aluminum on a further layer comprising mainly aluminum. The angle in which fluorescent X-rays propagate depends on the chemical species of the alloying element, as well as its direct surrounding within the host metal.

In a preferred embodiment, the device comprises at least different detection channels intended to receive fluorescent X-rays from each chemical element of the group comprising Cu, Mn, Zn, Fe. Herewith it is achieved that an intensity of fluorescent X-rays can be measured simultaneously of one or more of the alloying elements that are most often used within the core alloy. The device can thus be used to determine the attenuation of these fluorescent X-rays in a cladding that is located between the core and the X-ray directing and detecting means. This, in turn, provides the information needed to determine a cladding thickness. An advantage of the separate detection channels is that the device is very versatile to measure clad and cladding layer thickness on many brazing sheet products, or other coated aluminum products, wherein the alloying elements may vary from one product to another. A further advantage of the separate detection channels is that a choice can be made during operation which detector is most appropriate to utilise in the analysis. The device may comprise means for choosing which detector is most appropriate to utilise in the analysis.

In a further aspect of the invention it relates to the use of the device according to the invention for determining an intensity of element specific fluorescent X-rays emanating from a metal layer in which the fluorescent element is present in a concentration less than or equal to 20%. The device according to the invention is especially suitable for determination of the thickness of a layer or a sublayer comprising mainly a certain metal species, on a further layer comprising mainly the same metal species, and is also able to measure the thickness layers of disparate metals.

In particular, the invention further relates to the use of the device according to the invention for measurement of the thickness of a metal layer, comprising one or more sublayers, on a second layer comprising mainly aluminum alloy.

The invention further relates to the use of the device according to the invention for measurement of the thickness of a layer of aluminum alloy, comprising one or more sublayers, on a second layer comprising mainly aluminum alloy. The device as set out above is suitable for characterisation of, amongst others, aluminum sheets such as brazing sheet. The device is robust, and suitable for use in a production environment.

BRIEF DESCRIPTION OF THE DRAWINGS

The invention will now be explained using an example of a device that has been optimised for use in an aluminum brazing sheet facility, with reference to the drawing where FIG. 1 shows a schematic cross-sectional view of the device according to the invention during operation;

FIG. 3 shows a schematic top view inside of an integrated measuring unit comprising means for generating and directing a beam of primary X-rays, and means for detecting fluorescent X-rays;

FIG. 7 shows an example of a sheet identification memory content;

FIG. 8 shows an example of a visual user interface;

DESCRIPTION OF THE PREFERRED EMBODIMENTS

Figures 2, 4:
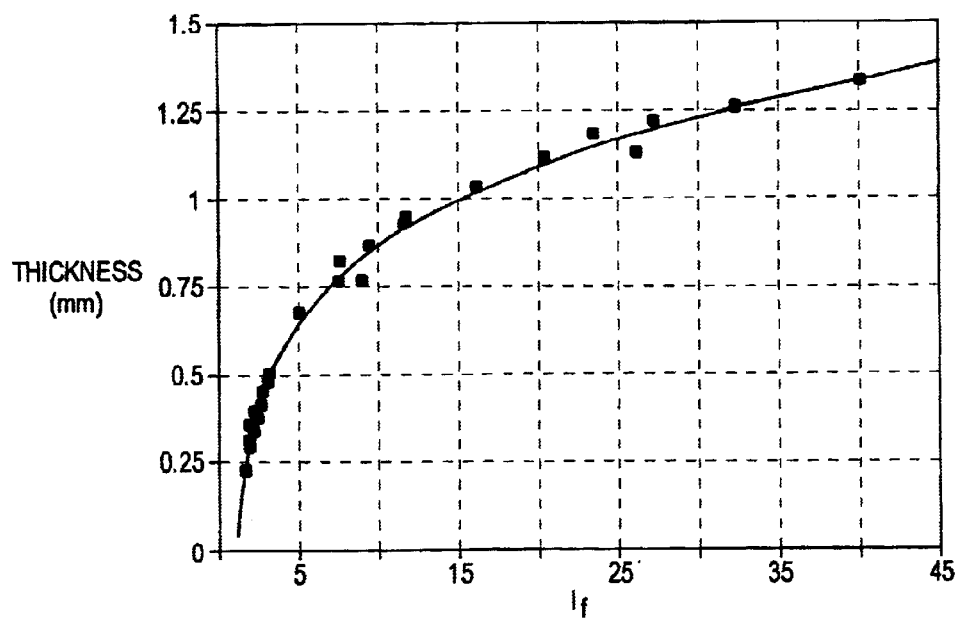
FIG. 2 shows a table of properties of fluorescent X-rays specific for some chemical elements.
FIG. 4 shows an experimental relation between the intensity factor of Mo-i fluorescent X-rays and thickness of brazing sheet.

FIG. 1 schematically shows a cross-sectional view of the device according to the invention. It comprises a backing (1), means (2) for generating and directing a primary beam of primary X-rays (3) on a metal sheet (4), and means (51, 52) for detection and determination of an intensity of element specific fluorescent X-rays (61, 62), also known in the art as XRF, or X-ray induced fluorescence. The metal sheet is depicted in cross section, and its thickness is greatly exaggerated in the drawing, in order to make visible some of the layers within the sheet. The means for directing the beam of primary X-rays may comprise an X-ray source as conventionally known in the art. For instance, a 30 kV X-ray tube comprising a tungsten target has been found to provide an excellent source of polychromatic X-rays, suitable to excite fluorescent X-rays in most alloying elements in aluminum. XRF radiation is spectrally characteristic for the element that emits the fluorescence, and therewith transmitted with a peaked angular distribution. This is indicated in FIG. 1, where an element comprised in the backing (1) characteristically emits fluorescent X-rays at angles peaking around $\alpha_1$, while an element comprised in a layer of the metal sheet may characteristically emit at angles peaking around a different angle of $\alpha_2$. It is presently understood that this is a manifestation of Bragg's law, and the local density of states (within the alloying complex) that enters Fermi's Golden Rule. The detecting means are placed such as to selectively receive the characteristic fluorescence of preselected elements, i.e., to selectively receive the fluorescence that emanates under a preselected angle with respect to the primary beam. Elementspecific fluorescence of elemental $K_\alpha$, levels is usually quite suitable for this purpose. In FIG. 2 a table is presented that contains properties of fluorescent X-rays of the $K_\alpha$, type of Mn, Fe, Cu, Zn and Mo. From the table the alignment angles of the means for detection at which optimum detection is achieved may be inferred.

The means for detecting fluorescent X-rays, and for measuring the intensity thereof, may be chosen according to what is generally known in the art. They may comprise a collimator, a dispersion crystal (such as LiF), and a proportional counting device. A detection channel comprising a sealed proportional counting tube is found to be very suitable. The means for directing and detecting X-rays may be comprised into a (translatable) integrated unit (11), furnished with an X-ray window (8).

In the art, there are two general methods of using XRF radiation to measure the thickness of sheet material or the thickness of a first layer of material on top of a second layer: (a) a method disclosed in U.S. Pat. No. 2,926,257 in which the intensity of fluorescence of the layer under analysis itself it approximately proportional to the thickness of that layer, and (b) a method disclosed in U.S. Pat. No. 2,711,480, in which the attenuation in the layer or sheet under investigation of fluorescence of an underlying layer or backing is a measure for the thickness.

The invention provides a device that is in principle capable of following both methods, depending on the mathematics with which the measured intensities are processed and interpreted. For purposes of further explanation, it is assumed that the device is applied to perform method (b). Referring to FIG. 1, the thickness of the metal sheet (4) is thus derived from the attenuation within the metal comprised in the sheet of XRF radiation (61) of fluorescent elements comprised in the backing (1). If the metal sheet comprises disparate layers, for instance a core (42) on both sides surrounded by clad layers (41, 43), the thickness of a cladding (41) sandwiched between the core and the means for directing and detecting may be determined analogously using fluorescence (62) of elements, for instance alloying elements, comprised in the core (42).

Attenuation of X-rays in matter is quantified by published attenuation and absorption coefficients for specific materials and X-ray wavelengths. In general, attenuation of X-rays propagating over a certain distance is described by the law of Lambert-Beers. In order to extract a correct value for the layer thickness from an intensity ratio of XRF radiation before and after propagation through the layer, accurate chemical analysis of the metal sheet, and/or correct values for the absorption coefficient and density of the metal sheet are required. Therefore, in practice, the device comprises means for memorising calibration data.

FIG. 3 shows a schematic top-view of the lay-out inside an integrated measuring unit with five detection channels (51, 52, 53, 54, 55) arranged radially around an X-ray window (8). In reality, fewer or more detection channels may be used. Each detection channel is aligned with respect to the beam of primary X-rays such as to selectively receive fluorescence characteristic of one pre-selected element, for instance of the $K_\alpha$ type, which propagates through the metal sheet at a characteristic angle. In a device that is designed for measurement of aluminum brazing sheet, the detection channels may comprise an individual channel for each of the elements Mo (51), Mn (52), Cu (53), Zn (54), Fe (55), or other elements that are expected to be used as an alloying element or a major constituent of one of the layers.

FIG. 4 shows an example of calibration data that may be memorised in the device. Laboratory measurements of the intensity ratio IF of Mo-$K_\alpha$ fluorescence were performed on a series of aluminum sheets, that were placed on a Mo backing and measured using a device in accordance with the invention. The thickness of the test sheets was measured independently using a metallographic/optical method as set out above, and ranged from 0.24 to 1.34 mm. Then the intensity ratio was measured. For each test sheet the thickness was plotted in the graph shown in FIG. 4 against the intensity ratio. As can be seen, the intensity ratio for the studied thickness range varied from 1.7 to 40.5 in a smooth monotonic function. Note that the wavelength of Mo-Ks radiation is believed to be sufficiently far away from absorption resonances within most Al-alloys, in particular most brazing sheets, that the attenuation coefficient for Mo-$K_\alpha$ radiation is believed to be independent of the alloy composition within the accuracy of the measurement.

The drawn line in FIG. 4 is the result of a fit to an equation of the form:

$$Thickness = a + b \cdot IF + c \cdot ln(IF) + d \cdot exp(-IF),$$

in which a, b, c, and d are experimentally determined parameters. As can be seen, the line accurately describes the experimental data.

Figure 5:
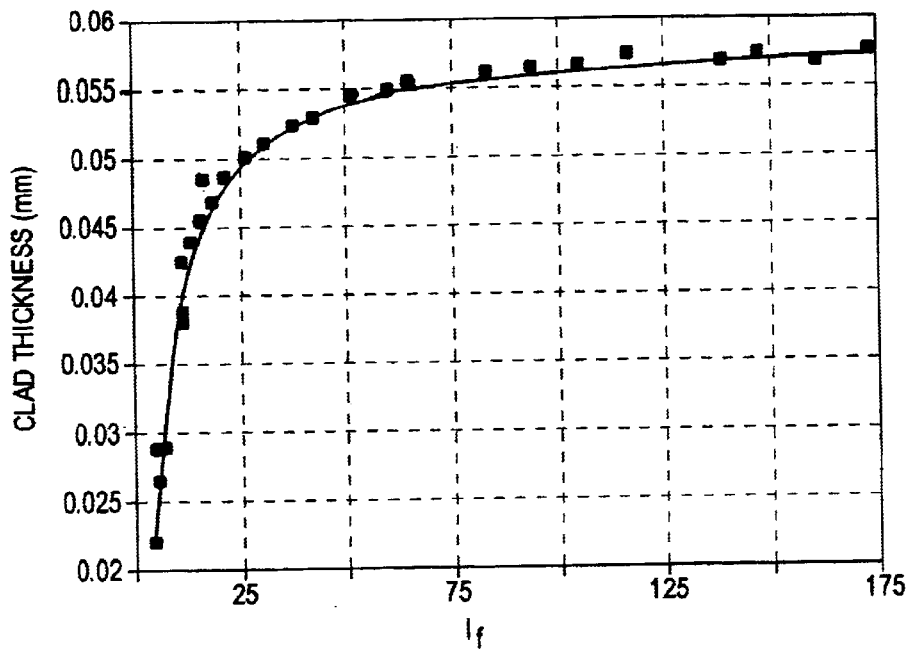
FIG. 5 shows an experimental relation between the intensity factor of Mn-K, fluorescent X-rays and thickness of a cladding layer in brazing sheet.

FIG. 5 shows an example of calibration data for a cladding (41) thickness measured using a device according to the invention on a series of aluminum brazing sheets. In this case, a brazing sheet with a core (42) comprising a Mn-containing alloy was used, and the intensity ratio of Mn-$K_\alpha$ fluorescence was determined as a function of cladding (41) thickness. A cladding thickness of 0.022 mm corresponds to an IF of 4.0, while 0.057 mm corresponds to an IF of 175, and in between a monotonously varying behaviour was observed. As can be seen, the Mn-$K_\alpha$ fluorescence attenuation in Al alloy is much stronger than that of Mo-$K_\alpha$ fluorescence.

Figure 6:
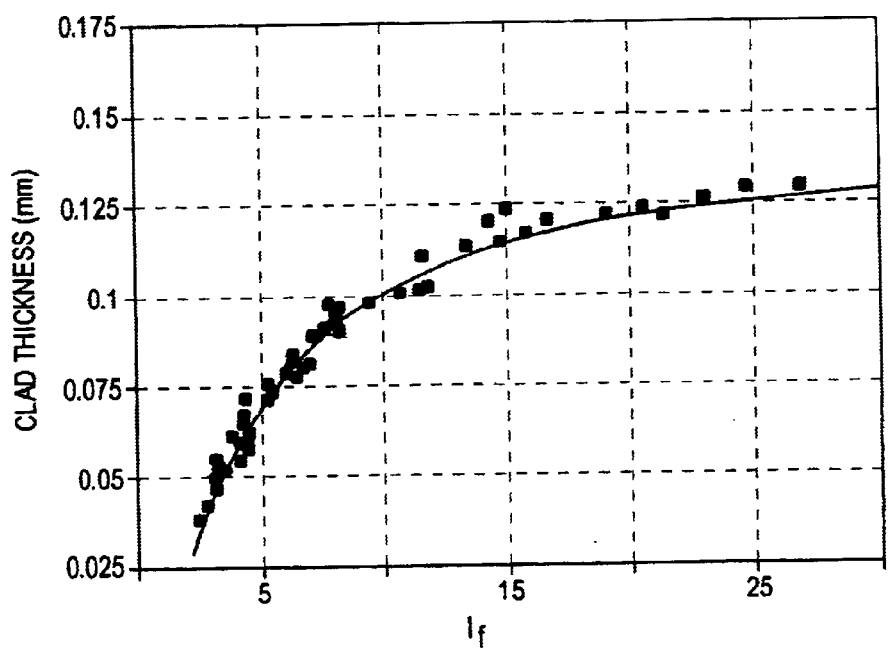
FIG. 6 shows an experimental relation between the intensity factor of Cu-Ks fluorescent X-rays and thickness of a cladding layer in brazing sheet.

FIG. 6 shows an example of calibration data for cladding thickness measured in the same way as FIG. 5, using a Cu-detection channel instead of a Mn-detection channel. As can be seen, a cladding thickness of 0.040 mm corresponds to IF of 3.8 while a cladding thickness of 0.130 mm corresponds to an IF of 27.

The drawn lines in FIGS. 5 and 6 are best fits according to an equation of the form:

$$Thickness = a \cdot exp(b/IF),$$

in which a and b are experimentally determined parameters. This form describes the measured data quite satisfactorily, as can be seen in FIGS. 5 and 6. Nevertheless, it is not excluded that other forms may be useful to describe this relationship between thickness and IF.

In order for the device to obtain a value for IF, a reference intensity must be known. A reference intensity for a cladding thickness measurement in a metal sheet could, for instance, be determined in a specimen which has the cladding removed. However, it is preferred that a value for a reference intensity is obtained from a measurement of the full sheet, since that does not involve removing a layer from the remainder of the sheet. To this extent, the device preferably disposes of means for computing a reference intensity by taking into account the concentrations of fluorescent elements inside the metal sheet (for instance a core and a cladding) and the intensity of primary X-rays as well as the intensity of backing-related fluorescent radiation that is emitted into the metal sheet, since both the primary X-rays and the backing-related fluorescent X-rays may be absorbed by fluorescent elements inside the metal sheet to be converted into fluorescent X-rays characteristic of these elements. Such effects must also be taken into account when the device is applied in method (a) as defined above.

Additionally, a number of other correction factors may be taken into account, including background noise and an influence of identical fluorescent elements in other layers.

For this purpose, the device may comprise means for storing an identifying label and a corresponding standard result for a plurality of standard metal sheets. FIG. 7 shows a number of records that may be comprised in the means for storing, which may for instance be accessed using a computer. The figure shows various fields within a record, i.e., name, core-type, and standard detection count rates for Mn, Cu, Zn, and Fe-related fluorescent X-rays. The standard count rates may have been determined experimentally, using a device according to the invention, in combination with independent means of characterisation. In an embodiment of the device according to the invention, it determines count rates for some fluorescent elements present in the metal sheet under investigation, for instance using the various detection channels as shown in FIG. 3. The device then compares the determined count rates to the standard values in the memory, for instance by using a least squares routine or another criterion. The resulting best matching type of metal sheet in the memory may then be displayed on an information unit, of which an example is given in FIG. 8.

As can be seen in FIGS. 5 and 6, the attenuation of Cu-K$_\alpha$, fluorescence in an aluminum-alloy cladding is less strong than that of Mn-K$_\alpha$. Depending on, for instance, which elements are present in the core alloy and in the clad alloy, and depending on, for instance, their respective concentrations, and depending on, for instance, the thicknesses of the layers, a decision can be made on which detector channel to use. In some cases this decision is obvious, but when dealing with a great variety of product specifications this becomes harder. For example, Mn is found to be a suitable fluorescent element for cladding thickness measurement of up to 0.04 mm, when the amount of Mn in the core alloy is higher than 0.5% by weight. However, Mn is often also present in a clad layer, and if the amount of Mn in the clad layer is too high, the fluorescence of Mn in the cladding will dominate the signal determined in a Mn-fluorescence detection channel. The thickness results will become inaccurate or even erroneous, but this is hard for an operator to recognise. Therefore, it is preferred that the device comprises computing means for deciding which fluorescent alloying element to use for obtaining layer thickness, without intervention of an operator.

Figure 9:
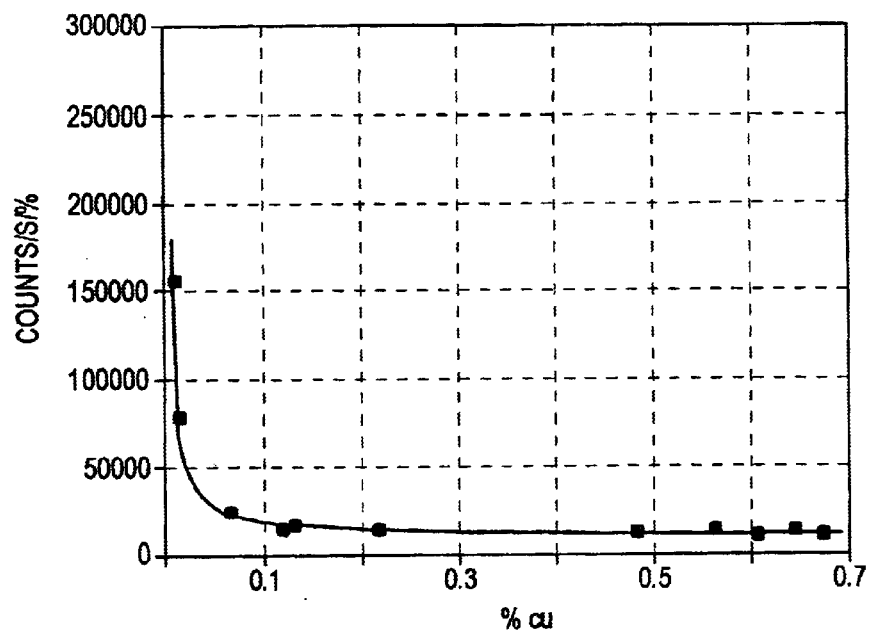
FIG. 9 shows an example of an experimentally determined sensitivity curve for Cu in aluminum.
Figure 10:
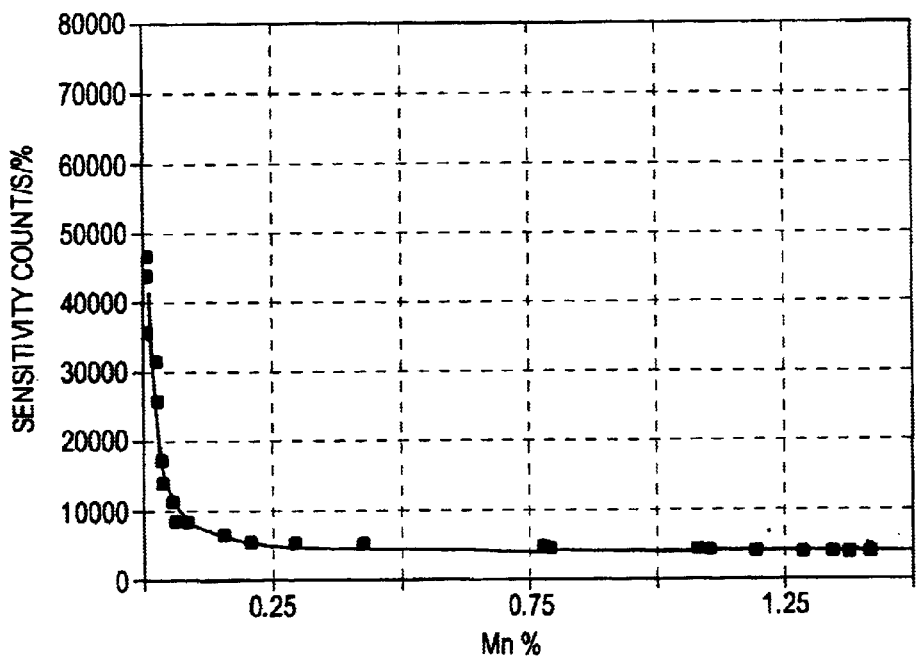
FIG. 10 shows an example of an experimentally determined sensitivity curve for Mn in aluminum.

To take full advantage of the entire dynamic range that is available in the detection channels, the output thereof may be normalised using an experimentally determined transfer function, or sensitivity curve. This sensitivity curve governs the relationship between fluorescent X-ray detection and the weight fraction of the fluorescing element question, or count rate per weight percent of the element. This enables the system to operate not only when the detector response linear but also when it is not linear, especially when the abundance of fluorescent elements in an alloy, or their fluorescence efficiency, is low, or the layers are strongly absorbing or thick. Examples of sensitivity curves are shown in FIGS. 9 and 10, for Cu and Mn respectively. The data in the figures has been experimentally determnined. As can be seen in FIG. 9, the count rate per percentage of Cu in an aluminum alloy is approximately constant when the concentration of Cu exceeds approximately 0.2%. However, a non-linear range begins when the concentration of Cu is lower than approximately 0.2%. The count rate per %Cu is observed to increase strongly below 0.2%. This is particularly important when compensating for the fluorescence of very low amounts of Cu within a cladding that adds to the fluorescence intensity of the Cu in the core with a different weight factor. A qualitatively similar behaviour can be seen for the sensitivity factor of Mn in Al (FIG. 10). However, the concentration of Mn below which the non-linear response sets in is about 0.5%. The drawn lines in FIGS. 9 and 10 are best fits to an equation of the form:

$$Sensitivity = a + b/5\%,$$

where a and b are fit parameters, and % denotes the concentration of the fluorescing element.

The device according to the invention may be used for determination of several clad layer thicknesses. For this the device would select an appropriate fluorescent element for each clad layer in the cladding, depending on, for instance, the relative abundance of the fluorescent elements in every layer, using a methodology as described above. Then after determining the intensity of fluorescence from each layer, the thickness of the layers above that layer can be extracted using the calibration curves.

What is claimed is:

1. A device for measurement of the thickness of a first layer, comprising one or more sublayers, on a second layer of a metal sheet by X-ray fluorescence analysis, said device for measurement comprising:

(a) means defining a specimen plane for supporting the metal sheet;
    (b) means for generating and directing a beam of polychromatic primary X-rays, said beam being able to penetrate into the first and second layers for converting primary X-rays into chemical element specific fluorescent X-rays by means of absorption of primary X-rays and re-emission of fluorescent X-rays by the chemical element; and
    (c) means for detecting element specific fluorescent X-rays and determining an intensity thereof, wherein the means for detection has been placed at an angle with respect to the primary beam of X-rays in dependence of the chemical element from which the fluorescent X-rays are to be detected.

2. The device according to claim 1, wherein said device comprises at least two different detection channels placed at an angle to receive fluorescent X-rays from different chemical elements.

3. The device according to claim 2, wherein said means for directing the beam of primary X-rays is placed such that the beam of primary X-rays is directed substantially perpendicular to the specimen plane.

4. The device according to claim 2, wherein said means for directing a beam of primary X-rays and the means for detecting element specific fluorescent X-rays are integrated into one measuring unit.

5. The device according to claim 2, further comprising means for storing an identifying label and a corresponding standard result for a plurality of standard metal sheets, and means for processing and comparing a measurement of at least one fluorescent X-ray intensity to the standard to find the identifying label of the standard metal sheet that best matches the measurement.

6. The device according to claim 2, wherein the means for supporting the metal sheet comprises a backing for converting primary X-rays into backing specific fluorescent X-rays by means of absorption of primary X-rays and re-emission of fluorescent X-rays by the backing, wherein the backing is located such that the metal sheet is placeable between the means for generating and directing a beam of polychromatic primary X-rays and the backing.

7. The device according to claim 2, wherein the device comprises at least a detection channel for receiving fluorescent X-rays specific for at least one chemical element of a group consisting of Cu, Mn, Zn, and Fe, in a metal layer comprising mainly Al.

8. The device according to claim 1, wherein the device comprises, for each chemical element of the group consisting of Cu, Mn, Zn, and Fe, a corresponding, separate channel intended to receive fluorescent x-rays from a corresponding one of each of said chemical elements.

9. The device according to claim 1, wherein said means for directing a beam of primary X-rays and the means for detecting element specific fluorescent X-rays are integrated into one measuring unit.

10. The device according to claim 9, further comprising means for pressing the measuring unit toward the specimen plane.

11. The device according to claim 1, further comprising means for storing an identifying label and a corresponding standard result for a plurality of standard metal sheets, and means for processing and comparing a measurement of at least one fluorescent X-ray intensity to the standard to find the identifying label of the standard metal sheet that best matches the measurement.

12. The device according to claim 1, wherein the means for supporting the metal sheet comprises a backing for converting primary X-rays into backing specific fluorescent X-rays by means of absorption of primary X-rays and re-emission of fluorescent X-rays by the backing, wherein the backing is located such that the metal sheet is placeable between the means for generating and directing a beam of polychromatic primary X-rays and the backing.

13. The device according to claim 12, wherein the device comprises an individual detection channel for receiving fluorescent X-rays specific for the backing.

14. The device according to claim 12 wherein the backing comprises the element molybdenum.

15. The device according to claim 1, wherein the device comprises at least a detection channel for receiving fluorescent X-rays specific for at least one chemical element of a group consisting of Cu, Mn, Zn, and Fe, in a metal layer comprising mainly Al.

16. The device according to claim 1, wherein the device comprises, for each chemical element of the group comprising Cu, Mn, Zn, and Fe, a corresponding, separate channel intended to receive fluorescent x-rays from a corresponding one of each of said chemical elements.

17. A method of using the device according to claim 1, said method comprising determining an intensity of element specific fluorescent X-rays emanating from a metal layer in which a fluorescent element is present in a concentration less than or equal to 20%.

18. A method of using the device according to claim 1, said method comprising measuring the thickness of a metal layer, comprising one or more sublayers, on a second layer comprising mainly aluminum alloy.

19. A method of using the device according to claim 1, and method comprising measuring the thickness of a layer of aluminum alloy, comprising one or more sublayers, on a second layer comprising mainly aluminum alloy.

20. The device according to claim 1, the device comprises at most one means for detecting per chemical element and the at least one means for detecting is a single detection channel.

21. The device according to claim 20 wherein said angle at which said single detection channel is placed corresponds to an exit angle characteristic of a wavelength of said fluorescent X-rays emitted by said chemical element.

22. The device according to claim 1, wherein said angle at which said detecting means is placed corresponds to an exit angle characteristic of a wavelength of said fluorescent X-rays emitted by said chemical element.

23. A method of measuring the thickness of a first layer, comprising one or more sublayers, on a second layer of a metal sheet by X-ray fluorescence analysis, by means of a device for measurement comprising (i) means defining a specimen plane for supporting the metal sheet, (ii) means for generating and directing a beam of polychromatic primary X-rays, said beam being able to penetrate into the first and second layers for converting primary X-rays into chemical element specific fluorescent X-rays by means of absorption of primary X-rays and re-emission of fluorescent X-rays by the chemical element, and (iii) means for detecting element specific fluorescent X-rays and determining an intensity thereof, wherein the means for detection has been placed at an angle with respect to the primary beam of X-rays in dependence of the chemical element from which the fluorescent X-rays are to be detected, said method comprising:

(a) defining a specimen plane for supporting said metal sheet;

(b) generating and directing said beam of polychromatic primary X-rays into the first and second layers so as to convert the primary X-rays into said chemical element specific fluorescent X-rays; and (c) detecting said element specific fluorescent X-rays with the means for detection placed at the angle with respect to the primary beam of X-rays in dependence of the chemical element from which the fluorescent X-rays are to be detected and determining said intensity thereof.

24. The method according to claim 23, wherein the means for supporting the metal sheet comprises a backing for converting primary X-rays into backing specific fluorescent X-rays by means of absorption of primary X-rays and re-emission of fluorescent X-rays by the backing, wherein the backing is located such that the metal sheet is placeable between the means for generating and directing a beam of polychromatic primary X-rays and the backing, wherein an element comprised in the backing characteristically emits fluorescent X-rays at angles peaking at about $\alpha_1$ while an element comprised in a layer of the metal sheet characteristically emits at angese peaking at about $\alpha_2$, wherein $\alpha_1$ differs from $\alpha_2$.

25. A device for determining an intensity of chemical element specific fluorescent X-rays emanating from a metal layer of a metal sheet in which a fluorescent element is present in a concentration less than or equal to 20%, said device comprising:

(a) means for defining a specimen plane for supporting the metal sheet;

(b) means for generating and directing a beam of polychromatic primary X-rays, said beam being able to penetrate into the layer for converting primary X-rays into chemical element specific fluorescent X-rays by means of absorption of primary X-rays and re-emission of fluorescent X-rays by the chemical element; and (c) means for detecting element specific fluorescent X-rays and determining an intensity thereof, wherein the means for detection has been placed at an angle with respect to the primary beam of X-rays in dependence of the chemical element from which the fluorescent X-rays are to be detected.

26. The device according to claim 25, wherein said device comprises at least two different detection channels placed at an angle to receive fluorescent X-rays from different chemical elements.

27. The device according to claim 25, wherein said means for directing the beam of primary X-rays have been placed such that the beam of primary X-rays is directed substantially perpendicular to the specimen plane.

28. The device according to claim 25, wherein said means for directing a beam of primary X-rays and the means for detecting element specific fluorescent X-rays are integrated into one measuring unit.

29. The device according to claim 28, further comprising means for pressing the measuring unit toward the specimen plane.

30. The device according to claim 25, further comprising means for storing an identifying label and a corresponding standard result for a plurality of standard metal sheets, and means for processing and comparing a measurement of at least one fluorescent X-ray intensity to the standard to find the identifying label of the standard metal sheet that best matches the measurement.

31. The device according to claim 25, wherein the means for supporting the metal sheet comprises a backing for converting primary X-rays into backing specific fluorescent X-rays by means of absorption of primary X-rays and re-emission of fluorescent X-rays by the backing, wherein the backing is located such that the metal sheet is placeable between the means for generating and directing a beam of polychromatic primary X-rays and the backing.

32. The device according to claim 31, wherein the device comprises an individual detection channel for receiving fluorescent X-rays specific for the backing.

33. The device according to claim 31, wherein the backing comprises the element molybdenum.

34. A method of using the device according to claim 31, said method comprising determining a thickness of a metal sheet from an attenuation of re-emitted fluorescent X-rays, within the metal comprised in the metal sheet.

35. The device according to claim 25, wherein the device comprises at least a detection channel for receiving fluorescent X-rays specific for a chemical element of a group consisting of Cu, Mn, Zn, Fe, in a metal layer comprising mainly Al.

36. The device according to claim 25, wherein the device comprises for each chemical element of the group consisting of Cu, Mn, Zn, Fe, a corresponding separate channel intended to receive fluorescent X-rays from a corresponding one of each of said chemical elements.

37. A method of determining an intensity of chemical element specific fluorescent X-rays emanating from a metal layer of a metal sheet in which a fluorescent element is present in a concentration less than or equal to 20%, by means of a device according to claim 24, said method comprising:

(a) defining a specimen plane for supporting said metal sheet;

(b) generating and directing said beam of polychromatic primary X-rays into the layer so as to convert the primary X-rays into said chemical element specific fluorescent X-rays; and (c) detecting said element specific fluorescent X-rays with the means for detection placed at the angle with respect to the primary beam of X-rays in dependence of the chemical element from which the fluorescent X-rays are to be detected and determining said intensity thereof.

38. A method of using the device according to claim 25, said method comprising determining a thickness of a first layer, said first layer comprising one or more sub layers, on a second layer of a metal sheet, wherein a beam of polychromatic primary X-rays is directed into the first and second layers, and the thickness of the first layer is derived from an attenuation of element specific fluorescent X-rays of fluorescent elements comprised in the second layer, within the metal comprised in the first layer.

39. The method according to claim 38, wherein the second layer comprises mainly an aluminium alloy.

40. The method according to claim 38, wherein the first layer comprises an aluminium alloy.

* * * * *